(12) United States Patent
Yoneta

(10) Patent No.: US 11,740,228 B2
(45) Date of Patent: *Aug. 29, 2023

(54) PARTICLE SEPARATING AND MEASURING DEVICE, AND PARTICLE SEPARATING AND MEASURING APPARATUS

(71) Applicant: KYOCERA Corporation, Kyoto (JP)

(72) Inventor: Masashi Yoneta, Kagoshima (JP)

(73) Assignee: KYOCERA Corporation, Kyoto (JP)

( * ) Notice: Subject to any disclaimer, the term of this patent is extended or adjusted under 35 U.S.C. 154(b) by 315 days.

This patent is subject to a terminal disclaimer.

(21) Appl. No.: 17/279,665

(22) PCT Filed: Sep. 24, 2019

(86) PCT No.: PCT/JP2019/037301
§ 371 (c)(1),
(2) Date: Mar. 25, 2021

(87) PCT Pub. No.: WO2020/067025
PCT Pub. Date: Apr. 2, 2020

(65) Prior Publication Data
US 2022/0034864 A1  Feb. 3, 2022

(30) Foreign Application Priority Data

Sep. 27, 2018 (JP) ................. 2018-182299

(51) Int. Cl.
*G01N 33/49* (2006.01)
*B01L 3/00* (2006.01)
*G01N 15/14* (2006.01)

(52) U.S. Cl.
CPC ...... *G01N 33/491* (2013.01); *B01L 3/502761* (2013.01); *G01N 15/1459* (2013.01);
(Continued)

(58) Field of Classification Search
CPC .......... G01N 15/00; G01N 37/00; B03B 5/00; B01L 2200/026; B01L 2200/0652;
(Continued)

(56) References Cited

U.S. PATENT DOCUMENTS

2014/0261757 A1* 9/2014 Katsumoto ........ G01N 15/1404
137/268

FOREIGN PATENT DOCUMENTS

JP       2012-076016 A    4/2012

* cited by examiner

*Primary Examiner* — Jennifer Wecker
*Assistant Examiner* — Francis Paul Horvath
(74) *Attorney, Agent, or Firm* — Volpe Koenig

(57) ABSTRACT

A particle separating and measuring device of the present disclosure includes: a first flow path device including a post-separation flow outlet through which a first fluid containing specific particles to be separated flows out; and a second flow path device on which the first flow path device is placed and including a first flow inlet through which the first fluid flows in, the first flow path device in which the post-separation flow outlet is arranged in a lower surface is placed on the second flow path device in which the first flow inlet is arranged in an upper surface of a first region, the post-separation flow outlet and the first flow inlet are connected so as to face each other, and a size of an opening of the first flow inlet is larger than a size of an opening of the post-separation flow outlet.

8 Claims, 15 Drawing Sheets

(52) U.S. Cl.
CPC ..... *G01N 15/1484* (2013.01); *G01N 33/4915* (2013.01); *B01L 2200/0668* (2013.01); *B01L 2300/087* (2013.01); *B01L 2300/0809* (2013.01); *G01N 2015/149* (2013.01)

(58) Field of Classification Search
CPC ..... B01L 2200/0668; B01L 2300/0809; B01L 2300/0816; B01L 2300/0864; B01L 2300/087; B01L 2300/0874
See application file for complete search history.

F I G. 8
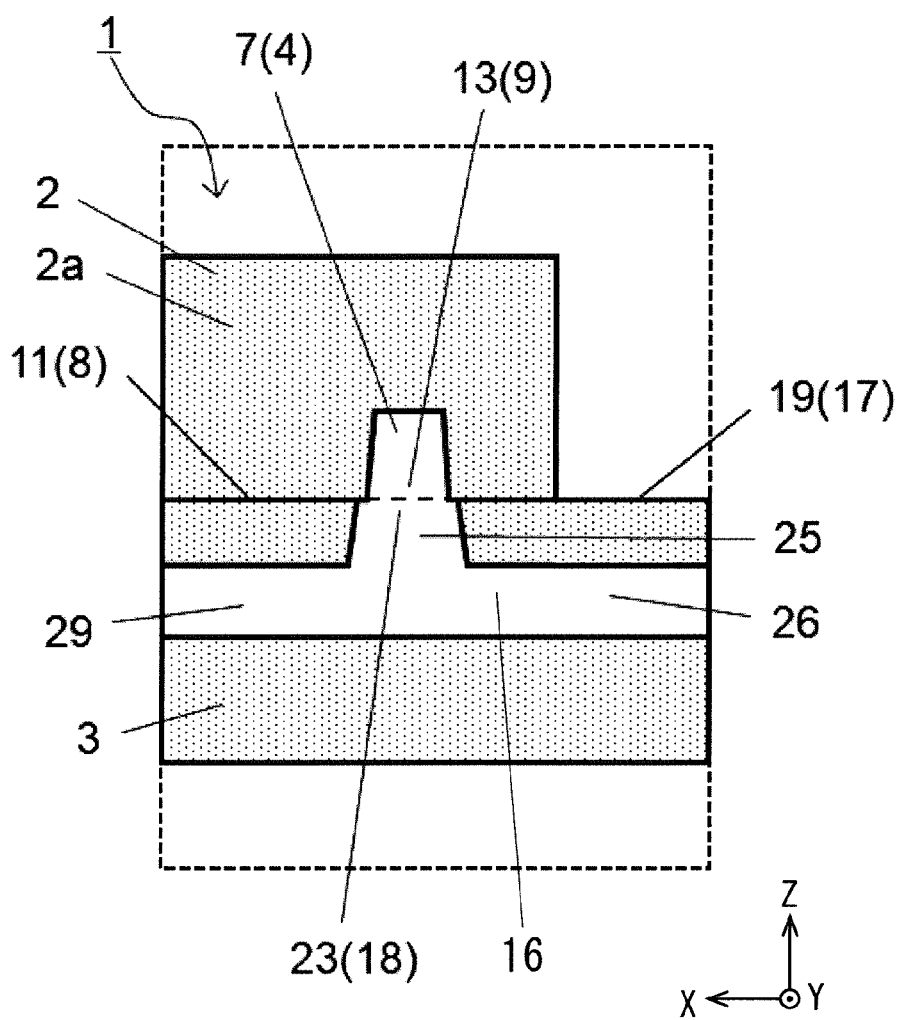

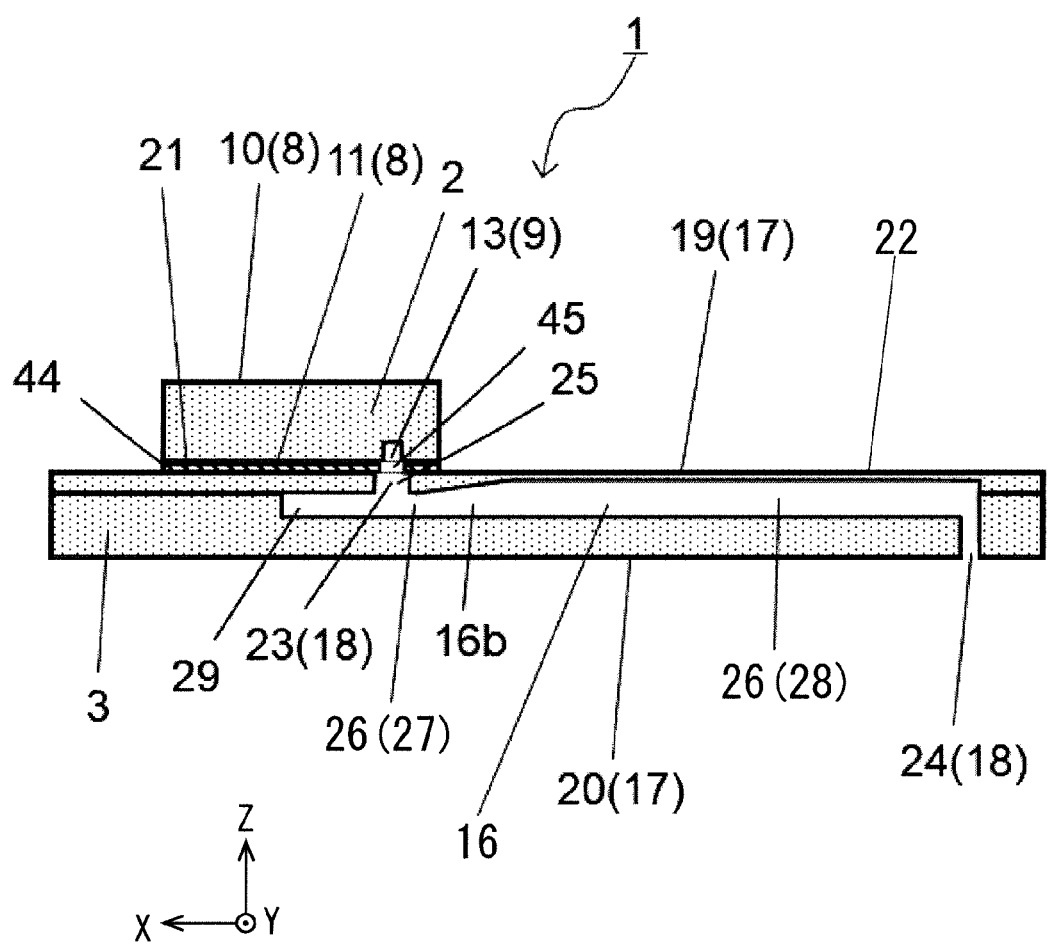
F I G. 1 1

F I G. 1 2
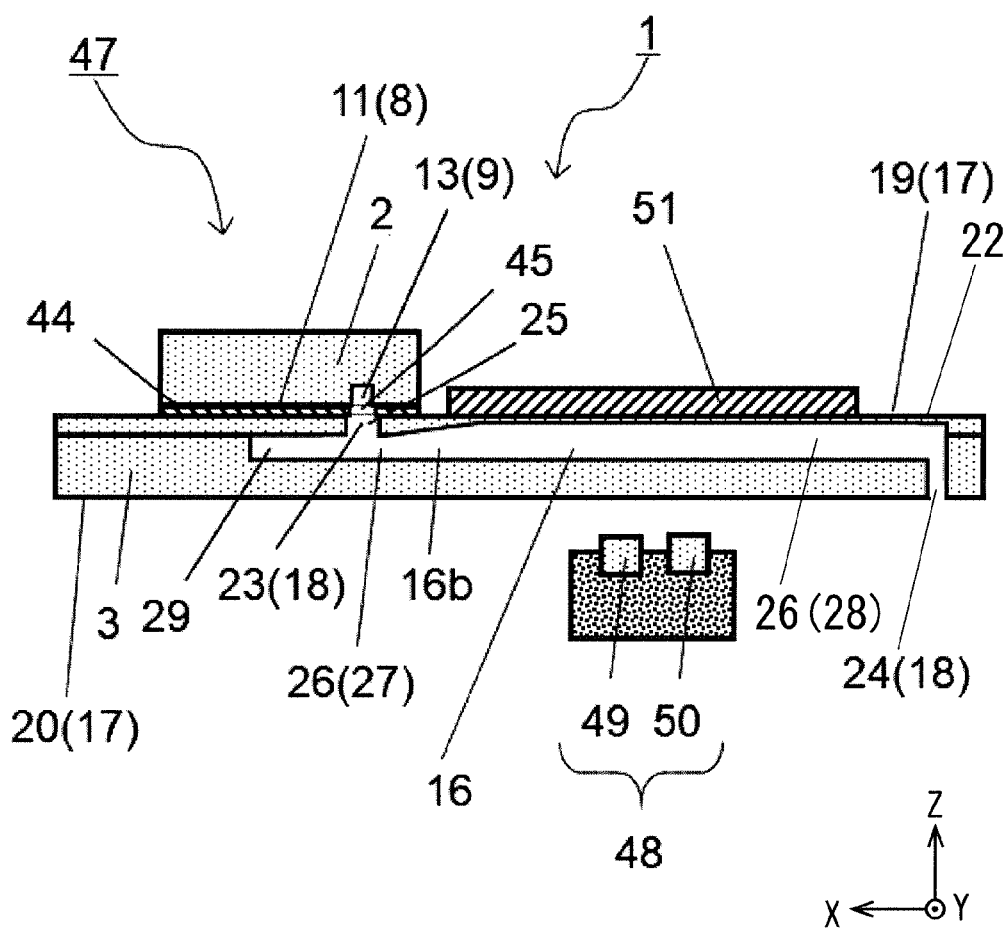

F I G. 1 3
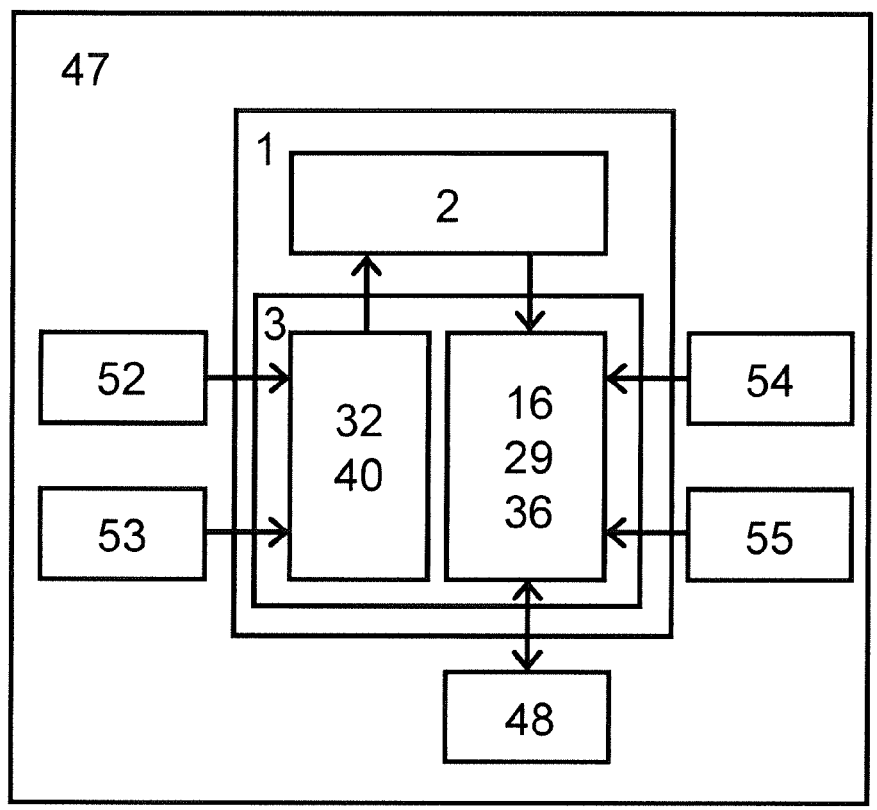

PARTICLE SEPARATING AND MEASURING DEVICE, AND PARTICLE SEPARATING AND MEASURING APPARATUS

CROSS-REFERENCE TO RELATED APPLICATION

The present application is a National Phase entry based on PCT Application No. PCT/JP2019/037301 filed on Sep. 24, 2019, entitled "PARTICLE SEPARATING AND MEASURING DEVICE, AND PARTICLE SEPARATING AND MEASURING APPARATUS", which claims the benefit of Japanese Patent Application No. 2018-182299, filed on Sep. 27, 2018, entitled "PARTICLE SEPARATING AND MEASURING DEVICE, AND PARTICLE SEPARATING AND MEASURING APPARATUS". The contents of which are incorporated by reference herein in their entirety.

FIELD

Embodiments of the present disclosure relate generally to a particle separating and measuring device and a particle separating and measuring apparatus used for separating specific particles from a plurality of types of particles contained in a liquid and measuring the specific particles.

BACKGROUND

A conventional particle separating device that separates and extracts particles in a liquid by using a minute flow path structure (micro flow path) including an inlet and a plurality of outlets and having a width of several μm to several hundred μm has been known. In such a particle separating device, for example, when a liquid (for example, blood) containing a plurality of types of particles (for example, red blood cells and white blood cells) is introduced from the inlet, desired particles (for example, white blood cells) in the liquid can be separated, and the desired particles and the other particles can be separately extracted from the plurality of outlets.

Thereafter, the type, number, concentration, optical characteristics or the like of the desired particles that have been separated and extracted is measured.

SUMMARY

A particle separating and measuring device, and a particle separating and measuring apparatus are disclosed. In one embodiment, a particle separating and measuring device includes: a first flow path device having a plate-like shape and including a pre-separation flow inlet through which a fluid flows in that contains specific particles to be separated, a main flow path connected to the pre-separation flow inlet, a plurality of branch flow paths each connected to the main flow path, and a post-separation flow outlet through which a first fluid flows out that contains the specific particles that have been separated; and a second flow path device having a plate-like shape and having a first region on which the first flow path device is placed, and a second region that serves as a measurement region for the specific particles, the second flow path device including a first flow inlet through which the first fluid flows in, a second flow inlet through which a second fluid not containing the specific particles flows in, a first flow path connected to the first flow inlet and through which the first fluid passes, and a second flow path connected to the second flow inlet and through which the second fluid passes, wherein the first flow path and the second flow path are arranged in the second region. Then, the post-separation flow outlet is arranged in a lower surface of the first flow path device, and is placed on the second flow path device to face and connect to the first flow inlet that is arranged in an upper surface of the first region of the second flow path device. A size of an opening of the first flow inlet is larger than a size of an opening of the post-separation flow outlet.

In one embodiment, a particle separating and measuring apparatus includes: the particle separating and measuring device described above; an optical sensor that irradiates a measurement unit of the first flow path and a measurement unit of the second flow path of the particle separating and measuring device with light, and receives light that has passed through the measurement unit of the first flow path and the measurement unit of the second flow path; and a control unit that measures the specific particles by comparing intensity of light, obtained by the optical sensor, that has passed through the measurement unit of the first flow path and intensity of light, obtained by the optical sensor, that has passed through the measurement unit of the second flow path.

BRIEF DESCRIPTION OF THE DRAWINGS

FIG. 8 illustrates a cross-sectional view showing a part of an example of the particle separating and measuring device according to an embodiment of the present disclosure.

FIG. 11 illustrates a cross-sectional view showing an example of the particle separating and measuring device according to an embodiment of the present disclosure.

FIG. 12 illustrates a cross-sectional view showing an example of the particle separating and measuring apparatus including the particle separating and measuring device according to an embodiment of the present disclosure.

FIG. 13 illustrates a block diagram schematically showing an example of an entire structure of the particle separating and measuring apparatus according to an embodiment of the present disclosure.

DETAILED DESCRIPTION

In order to separate desired particles in a liquid using a micro flow path, used is a particle separating device having a configuration in which a micro flow path having a configuration in which a plurality of branch flow paths are connected to a main flow path is used, and a sample that is a liquid containing a plurality of types of particles together with particles to be separated and a fluid that generates a pressing flow from the main flow path to the branch flow paths are allowed to flow in. Next, in order to measure the concentration and the like of the particles that have been separated by the particle separating device, a liquid containing the particles is subsequently allowed to flow into the particle measuring device and introduced into a flow path of a measuring unit, and measurement is performed. Then, in order to perform these pieces of operation in a series of procedures, a particle separating and measuring device in which the particle separating device and the particle measuring device are connected is used.

For this particle separating and measuring device, a particle separating and measuring device having a configuration advantageous for smoothly allowing a liquid containing particles that have been separated to flow from the particle separating device into the particle measuring device and reducing the occurrence of problems such as retention of particles at the connection part is desired.

Hereinafter, an example of a particle separating and measuring device of the present disclosure and a particle separating and measuring apparatus including the same will be described with reference to the drawings. In the present disclosure, for convenience, a rectangular coordinate system (X, Y, Z) is defined so that the positive side in a Z axis direction is upward, but any direction may be upward or downward. The contents below illustrate embodiments of the present disclosure, and the present disclosure is not limited to these embodiments.

(Particle Separating and Measuring Device)

Figure 1:
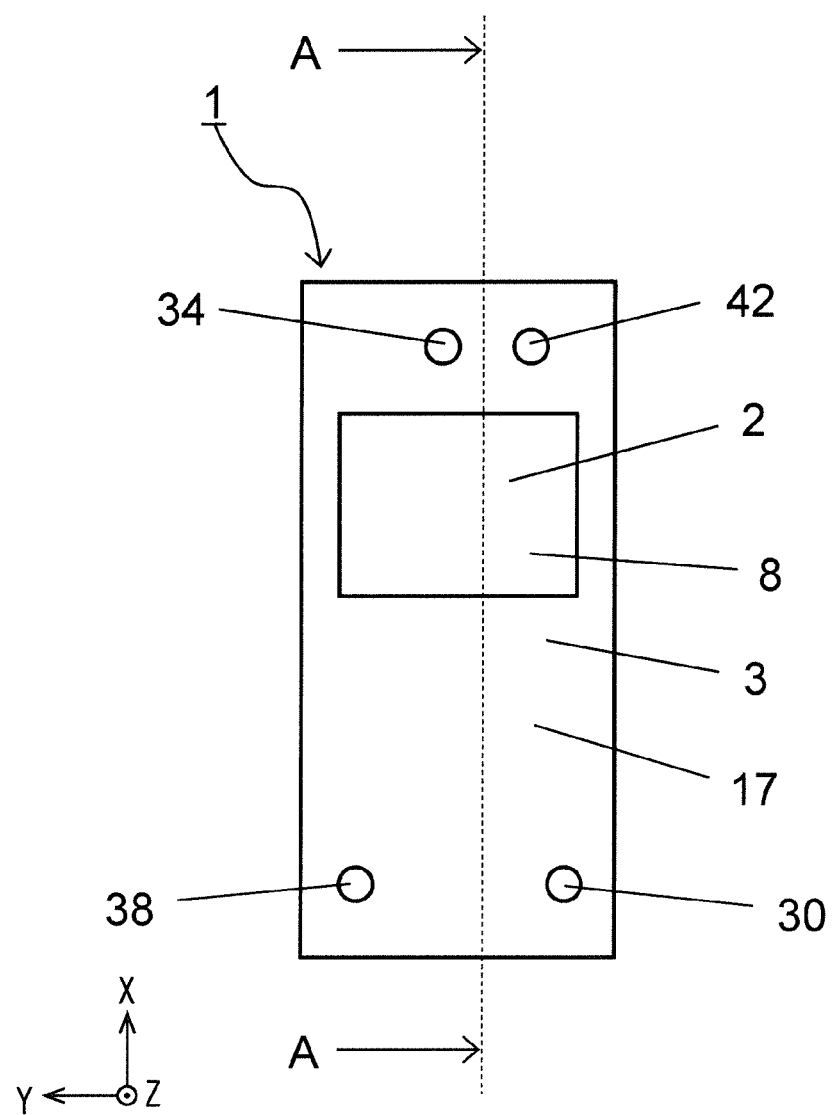
FIG. 1 illustrates a top view showing an example of a particle separating and measuring device according to an embodiment of the present disclosure.
Figure 2:
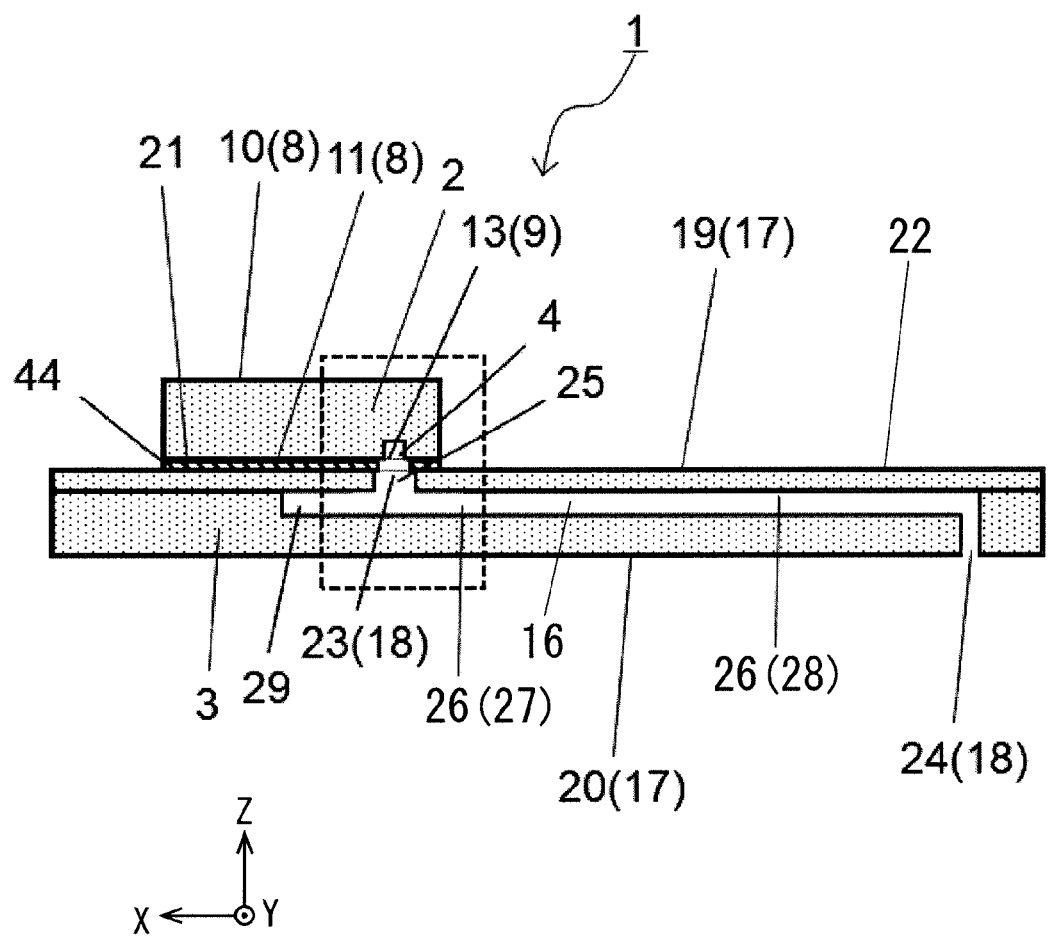
FIG. 2 illustrates a cross-sectional view showing an example of the particle separating and measuring device according to an embodiment of the present disclosure.

FIGS. 1 and 2 schematically illustrate an example of particle separating and measuring device according to an embodiment of the present disclosure. FIG. 1 is a top view of a particle separating and measuring device 1. FIG. 2 is a cross-sectional view of the particle separating and measuring device 1 cut along an A-A line in FIG. 1.

The particle separating and measuring device 1 allows a fluid (sample) containing specific particles to be separated to flow through a first flow path device 2 which is a particle separating device, so that particles to be separated which are the specific particles in the sample are separated and recovered. The specific particles (the particles that have been separated) are allowed to flow through a second flow path device 3 which is a particle measuring device connected to the first flow path device 2, so that the specific particles can be measured. For example, the particle separating and measuring device 1 can separate and recover white blood cells, which are specific components, from blood and measure the number of white blood cells.

Figure 3:
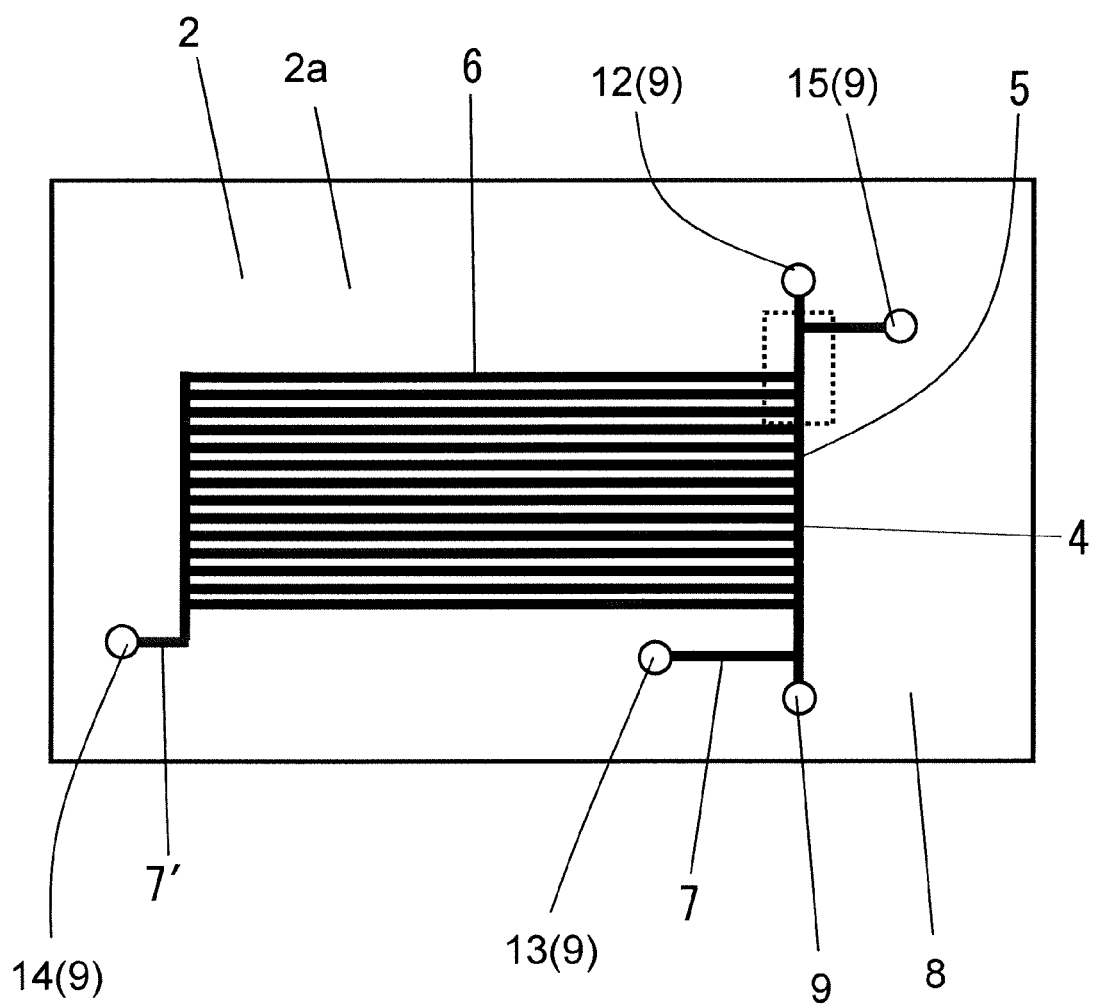
FIG. 3 illustrates a plan view showing an example of a first flow path device in the particle separating and measuring device according to an embodiment of the present disclosure.

FIG. 3 schematically illustrates an example of the first flow path device 2 which is a particle separating device. FIG. 3 is a plan view of the first flow path device 2 viewed from above.

(Particle Separating Device: First Flow Path Device)

The first flow path device 2 is a particle separating device capable of separating and recovering specific particles to be separated from a liquid (sample) containing a plurality of types of particles including the specific particles to be separated. The first flow path device 2 includes a pre-separation flow inlet 12 through which a fluid flows in that contains specific particles to be separated, a main flow path 5 connected to the pre-separation flow inlet 12, a plurality of branch flow paths 6 each connected to the main flow path 5, and a post-separation flow outlet 13 through which a first fluid flows out that contains the specific particles that have been separated.

The first flow path device 2 has a plate-like shape as a whole, and includes a separation flow path 4 inside a substrate 2a which has a plate-like shape. The separation flow path 4 includes the linear main flow path 5 and the plurality of branch flow paths 6 connected so as to branch from the main flow path 5. In the first flow path device 2 of the present disclosure, a sample (for example, blood) flowing in the first flow path device 2 flows into the main flow path 5, and particles (second particles, for example, red blood cells) different from specific particles (first particles, for example, white blood cells) flow from the main flow path 5 into the branch flow path 6, so that the specific particles (first particles) in the sample can be separated. Also, the second particles flow into the branch flow path 6 so that the second particles can be separated from the sample.

The branch flow path 6 is designed so that the second particles flow in by branching from the main flow path 5, but only the second particles do not always flow in. Particles (third particles or the like) different from the second particles flow into the branch flow path 6 in some cases.

Figure 4:
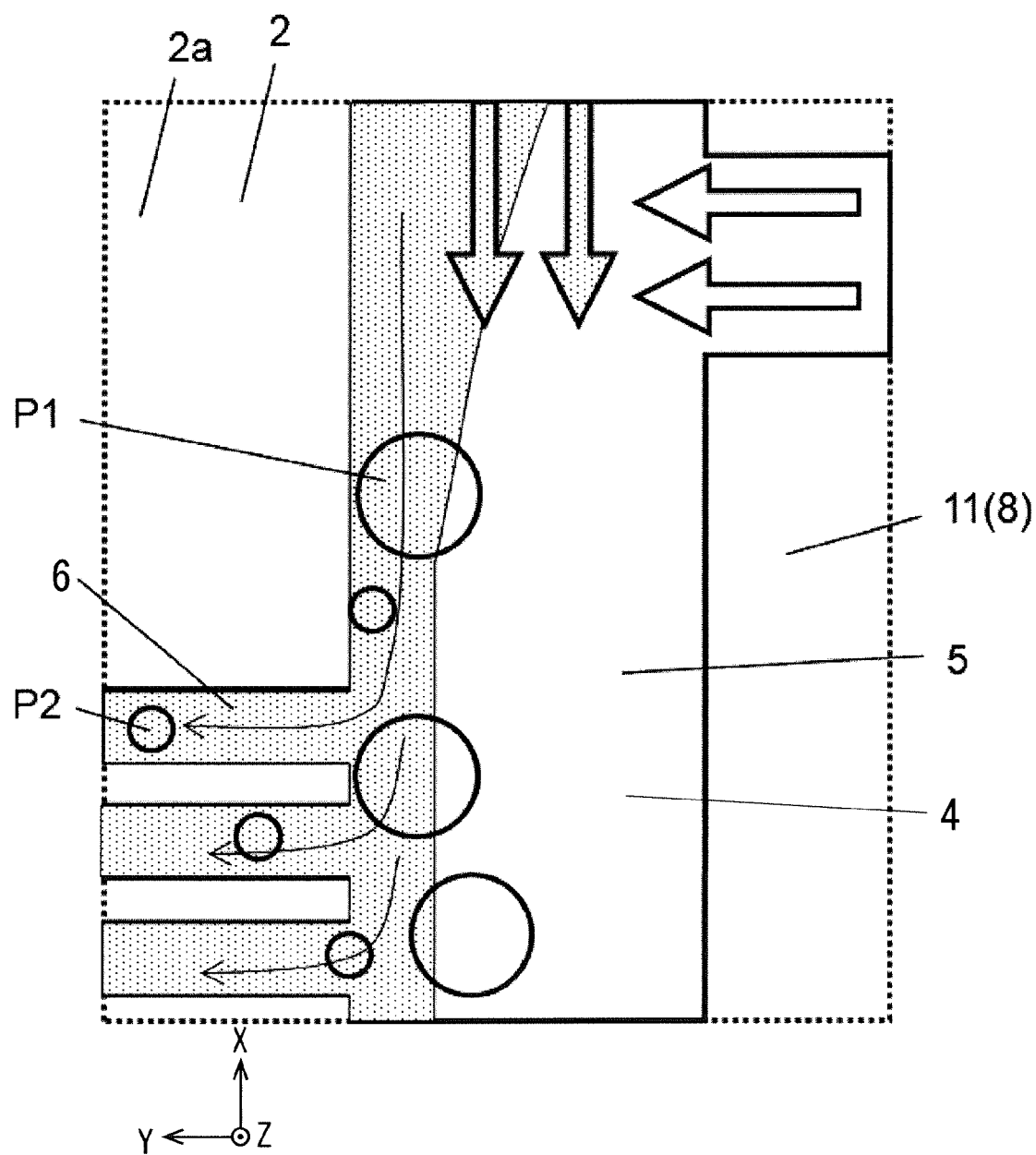
FIG. 4 illustrates a plan view showing a part of an example of the first flow path device in the particle separating and measuring device according to an embodiment of the present disclosure.

FIG. 4 schematically illustrates a process of separating the first particles and the second particles by the main flow path 5 and the branch flow paths 6. FIG. 4 is an enlarged plan view of a broken line section in FIG. 3. A large circle in FIG. 4 indicates a first particle P1 and a small circle indicates a second particle P2. A hatched arrow along the X axis direction indicates a main flow and a white arrow along the Y axis direction indicates a "pressing flow" described later. A hatched region in FIG. 4 indicates a "lead-in flow" described later.

The separation flow path 4 of the present disclosure includes one main flow path 5 and a plurality of branch flow paths 6 connected to a side surface in the middle of the one main flow path 5 in a direction orthogonal to the side surface. In the first flow path device 2, a sectional area and length of each of the main flow path 5 and the branch flow path 6, a flow rate of the sample and the like are adjusted, thus the "lead-in flow", which flows from the main flow path 5 into the branch flow path 6 can be generated in the main flow path 5. The first flow path device 2 generates the "pressing flow", which can press the sample flowing in the main flow path 5 against the branch flow path 6 side, in the separation flow path 4. As a result, as illustrated in FIG. 4, a width of the branch flow path 6 in which the lead-in flow flows is set to smaller than a size of the first particle P1 as the specific particle flowing in the sample and larger than a size of the second particle P2 as the other particle, thus the second particle P2 can be led in the branch flow path 6. Further, a width of the lead-in flow pressed by the pressing flow and flowing in the branch flow path 6 side in the main flow path 5 is set to larger than a barycentric position of the second particle P2 flowing in the sample and smaller than a barycentric position of the first particle P1, thus the second particle P2 can be effectively led in the first branch flow path 6. As a result, the first particles P1, which are specific particles in the sample, can be separated and recovered by being placed on a stream of the main flow path 5. At the same time, the second particles P2 can be separated from the sample and recovered by being placed on a stream of the branch flow path 6.

The first flow path device 2 of the present disclosure can be particularly suitably used for separating red blood cells and white blood cells in blood as a sample. The size of the red blood cell in blood is 6 µm to 8 µm, for example, and a barycentric position of the red blood cell in blood is located 2 µm to 2.5 µm from an edge thereof, for example. The size of the white blood cell is 10 µm to 30 µm, for example, and a barycentric position of the white blood cell is located 5 µm to 10 µm from an edge thereof, for example. In this case, it is sufficient that the main flow path 5 has the sectional area ranging from 300 µm$^2$ to 1000 µm$^2$ and the length ranging from 0.5 mm to 20 mm, for example. It is sufficient that the dimension of the cross section is within the range of the above cross-sectional area, for example, the width is about 30 µm and the height is about 20 µm. It is sufficient that the branch flow path 6 has the sectional area ranging from 100 µm$^2$ to 500 µm$^2$ and the length ranging from 3 mm to 25 mm, for example. It is sufficient that the dimension of the cross section is within the range of the above cross-sectional area, for example, the width is about 15 µm and the height is about 20 It is sufficient that the flow rate in the separation flow path 4 is 0.2 m/s to 5 m/s, for example. As a result, the width of the lead-in flow can be set to 2 µm to 10 µm, for example, thus the red blood cell and the white blood cell can be effectively separated from blood.

In addition to white blood cells and red blood cells, the specific particles may be, for example, various extracellular vesicles, such as exosomes (30 nm to 200 nm in size), microvesicles (200 nm to 1000 nm in size), or Large oncosomes (1 µm to 10 µm). The specific particles may be inorganic substances, or may be specific fine particles in a fluid such as a suspension containing fine powder. In either case, the shape and dimensions of the separation flow path 4 may be appropriately designed according to the size of specific particles to be separated.

The first flow path device 2 includes a plurality of first openings 9 opened on the upper surface and/or the lower surface of the substrate 2a. At least one of the first openings 9 is an inlet through which the sample flows into the main flow path 5. The inlet includes a pre-separation flow inlet 12 through which a sample that is fluid containing specific particles (for example, the first particles P1) to be separated flows toward the main flow path 5, and a pressing flow inlet 15, which is connected to a side surface of the main flow path 5 located on the upstream side of the plurality of branch flow paths 6 and opposite to the plurality of branch flow paths 6 in a direction orthogonal to the side surface of the main flow path 5, and through which a fluid to generate a pressing flow flows in.

In this case, it is sufficient that the first opening 9 as the pre-separation flow inlet 12 has a circular shape and a size of, for example, 1 mm to 3 mm. It is sufficient that the height of each flow path is set to the same height as the separation flow path 4, and the depth of the pre-separation flow inlet 12 is, for example, the depth from the opening in the upper surface of the substrate 2a to the bottom surface of the main flow path 5.

It is sufficient that the first opening 9 as the pressing flow inlet 15 has a circular shape and a size of, for example, 1 mm to 3 mm. It is sufficient that the height of the flow path for the pressing flow is set to the same height as the separation flow path 4, and the depth of the pressing flow inlet 15 is, for example, the depth from the opening in the upper surface of the substrate 2a to the bottom surface of the main flow path 5.

The separation flow path 4 further includes a recovery flow path 7 connected to the main flow path 5, and can recover the first particles P1 that have been separated, by the recovery flow path 7. In the separation flow path 4 in the present disclosure, the first particles P1 can be recovered in the recovery flow path 7 using the pressing flow.

The separation flow path 4 may include a disposal flow path 7' connected to the plurality of branch flow paths 6. The disposal flow path 7' may recover or dispose of the second particles P2 that have been separated in the branch flow path 6. When the second particles P2 are recovered by the plurality of branch flow paths 6, one disposal flow path 7' to which the plurality of branch flow paths 6 are connected functions as a flow path for recovering the second particles P2. In this case, the fluid containing the first particles P1 and flowing from the main flow path 5 to the recovery flow path 7 may be disposed of.

The first flow path device 2 is a member made of the substrate 2a which has a plate-like shape. The separation flow path 4 is arranged inside the substrate 2a which has a plate-like shape. The first flow path device 2 includes a pair of first upper and lower surfaces 8 located in the upper and lower portions in a thickness direction (the Z axis direction). The separation flow path 4 includes a plurality of first openings 9 located and opened in either surface or both surfaces of the pair of first upper and lower surfaces 8.

In the present disclosure, one of the pair of first upper and lower surfaces 8 is defined as a first upper surface 10 and the other one thereof is defined as a first lower surface 11 for descriptive purposes. In the pair of first upper and lower surfaces 8, the first upper surface 10 is a surface located on a positive side of the Z axis and the first lower surface 11 is a surface located on a negative side of the Z axis. In the present disclosure, at least one of the plurality of first openings 9 is located in the first lower surface 11.

The plurality of first openings 9 include the pre-separation flow inlet 12 through which the sample flows into at least the first main flow path 5, the post-separation flow outlet 13 through which a fluid containing the first particles P1 that are the specific particles and that have been separated, as a first fluid, flows from the first recovery flow path 7 and is recovered, and at least one disposal flow outlet 14 through which constituents in which the first particles P1 are removed from the sample are recovered. In the present disclosure, the first opening 9 includes the pressing flow inlet 15 through which the fluid for the pressing flow for pressing the sample against the branch flow path 6 side flows in. In the present disclosure, the disposal flow outlet 14 is connected to the main flow path 5 and the disposal flow path 7'. The fluid flowing out through the disposal flow outlet 14 is recovered through a through hole 14' formed in the second flow path device 3 described later.

A planar shape of the first flow path device 2 in the present disclosure is a rectangular shape. Each of the first upper and lower surfaces 8 is a flat surface. A planar shape of the first flow path device 2 is not limited to the rectangular shape.

Each of the first upper and lower surfaces 8 is not limited to the flat surface. In the first upper and lower surfaces 8, shapes of the first upper surface 10 and the first lower surface 11 may be different from each other.

The first flow path device 2 is formed of a material of polydimethylsiloxane (PDMS) or acrylic (PMMA), for example. It is sufficient that a thickness of the first flow path device 2 is 1 mm to 5 mm, for example. It is sufficient that the planar shape of the first flow path device 2 has a short side with a length of 10 mm to 20 mm and a long side with a length of 10 mm to 30 mm, for example, in the case of having a rectangular shape. The first flow path device 2 can be formed by preparing two substrates, forming a groove in one of the two substrates to serves as the separation flow path 4, and attaching the two substrates to each other to cover the groove so that the substrate 2a including the separation flow path 4 in the inside is obtained, for example.

(Particle Measuring Device: Second Flow Path Device)

The second flow path device 3 is a flow path device for measuring the specific particles separated and recovered in the first flow path device 2, and constitutes the particle separating and measuring device 1 together with the first flow path device 2. The second flow path device 3 has a first region 21 on which the first flow path device 2 is placed and a second region 22 that serves as a measurement region for specific particles, and includes a first flow inlet 23 through which a first fluid flows in, a second flow inlet through which a second fluid containing no specific particles described later flows in, a first flow path 16 connected to the first flow inlet 23 and through which the first fluid passes, and a second flow path, which will be described later, connected to the second flow inlet and through which the second fluid passes, the first flow path 16 and the second flow path being arranged in the second region 22. The second flow path device 3 is plate-shaped as a whole.

As illustrated in FIG. 2, the second flow path device 3 includes the first flow path 16 connected to the separation flow path 4 of the first flow path device 2. The second flow path device 3 has translucency. As a result, the second flow path device 3 allows the first fluid containing the specific particles separated and recovered in the first flow path device 2 to flow to the first flow path 16 and can measure the specific particles using an optical sensor described later. Specifically, the second flow path device 3 measures intensity of light passing through the first fluid containing the specific particles in the first flow path 16, thereby measuring the specific particles.

The second flow path device 3 is a member in which a flow path is formed in the inside of a plate-like substrate. The first flow path 16 is arranged inside the plate-like substrate. The second flow path device 3 includes a pair of second upper and lower surfaces 17 located in the upper and lower portions in a thickness direction (the Z axis direction). The first flow path 16 includes a plurality of second openings 18 located and opened in either surface or both surfaces of the pair of second upper and lower surfaces 17.

In the present disclosure, one of the pair of second upper and lower surfaces 17 is defined as a second upper surface 19 and the other one thereof is defined as a second lower surface 20 for descriptive purposes. In the pair of second upper and lower surfaces 17, the second upper surface 19 is a surface located on a positive side of the Z axis and the second lower surface 20 is a surface located on a negative side of the Z axis.

A planar shape of the second flow path device 3 in the present disclosure is a rectangular shape. Each of the second upper and lower surfaces 17 is a flat surface. A planar shape of the second flow path device 3 is not limited to the rectangular shape. Each of the second upper and lower surfaces 17 is not limited to the flat surface. In the second upper and lower surfaces 17, shapes of the second upper surface 19 and the second lower surface 20 may be different from each other.

The second flow path device 3 may be formed of acrylic (PMMA) or cycloolefin polymer (COP), for example. It is sufficient that a thickness of the second flow path device 3 is 0.5 mm to 5 mm, for example. It is sufficient that the planar shape of the second flow path device 3 has a short side with a length of 20 mm to 30 mm and a long side with a length of 20 mm to 60 mm, for example, in the case of having a rectangular shape. The second flow path device 3 can be formed by preparing two substrates, forming a groove in one of the two substrates to serve as the first flow path 16, and attaching the two substrates to each other to cover the groove so that the substrate including the first flow path 16 in the inside is obtained, for example.

Figure 5:
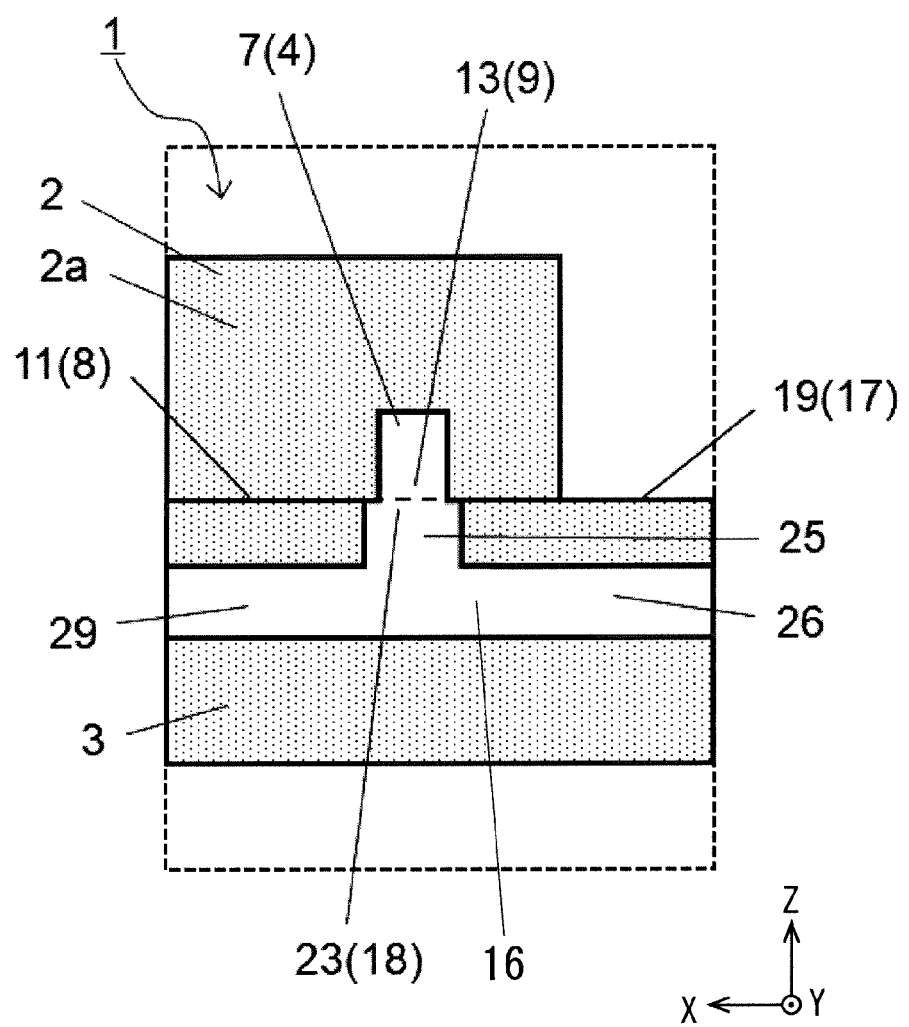
FIG. 5 illustrates a cross-sectional view showing a part of an example of the particle separating and measuring device according to an embodiment of the present disclosure.

FIG. 5 schematically illustrates a part of an example of the particle separating and measuring device 1 including the first flow path device 2 that is a particle separating device and the second flow path device 3 that is the particle measuring device. FIG. 5 is an enlarged view of a broken line section in FIG. 2.

In the second flow path device 3 in the present disclosure, at least one of the plurality of second openings 18 is located in the second upper surface 19. The first flow path device 2 is placed on the first region 21 of the second upper surface 19 with the first lower surface 11 facing the second upper surface 19, and the post-separation flow outlet 13 of the first opening 9 located in the first lower surface 11 and the first flow inlet 23 of the second opening 18 located in the second upper surface 19 are connected to each other. Accordingly, in the particle separating and measuring device 1 in the present disclosure, the flow path of the first flow path device 2 is directly connected to the flow path of the second flow path device 3, and the process from the separation and recovery to the measurement of the specific particles in the sample can be continuously performed, thus a work efficiency can be improved. The first flow path device 2 and the second flow path device 3 which have plate-like shapes are arranged to be stacked in the thickness direction, thus the particle separating and measuring device 1 can be minimized.

The second flow path device 3 of the present disclosure includes the first region 21 in which the first flow path device 2 is placed on the second upper surface 19 and the second region 22 that serves as a measurement region for specific particles. In a plan view, the first flow path 16 in the second flow path device 3 is arranged to extend from the first region 21 to the second region 22, and the first flow path device 2 is arranged only in the first region 21 of the second flow path device 3. As a result, since the first flow path 16 is located in the second region 22 so as not to overlap the first flow path device 2, the second region 22 can be used as a particle measurement region, and the first flow path 16 located in the second region 22 can be used as a measurement flow path.

In the particle separating and measuring device 1, a member which can reflect light may be arranged on the second region 22 as described later.

The first flow path device 2 may be formed of a material different from that of the second flow path device 3. In the present disclosure, for example, the first flow path device 2 is formed of PDMS and the like, and the second flow path device 3 is formed of COP and the like.

As is the case in the present disclosure, the first flow path device 2 is located on an upper side of the second flow path device 3. Specifically, the first flow path device 2 is located on the first region 21 of the second upper surface 19 of the second flow path device 3. As a result, the first fluid containing the specific particles separated and recovered in the first flow path device 2 can be efficiently flowed into the second flow path device 3 also using gravity, and a retention of the first fluid containing the specific particles midway through the flow path can be reduced.

The present disclosure does not exclude an embodiment in which the first flow path device 2 is arranged on the second lower surface 20 of the second flow path device 3.

The plurality of second openings 18 include a first flow inlet 23 through which the first fluid containing the specific particles separated flows into the first flow path 16 and a first flow outlet 24 through which the first fluid is recovered from the first flow path 16. The opening of the first flow inlet 23 is arranged in the second upper surface 19, and the first flow inlet 23 is connected to the post-separation flow outlet 13 of the first flow path device 2 while facing the post-separation flow outlet 13. The first flow outlet 24 is arranged in the second lower surface 20. As a result, by using the gravity, the first fluid can easily flow from the first flow path device 2 through the first flow inlet 23 and the first fluid can be easily recovered in the first flow outlet 24.

(Connection Structure Between First Flow Path Device and Second Flow Path Device)

The first flow path device 2 is placed on the first region 21 of the second upper surface 19 of the second flow path device 3. Then, the post-separation flow outlet 13 of the first flow path device 2 and the first flow inlet 23 of the second flow path device 3 are connected to each other so as to face each other. The second opening 18 of the first flow inlet 23 is larger than the first opening 9 of the post-separation flow outlet 13 as illustrated in FIG. 5. As a result, the retention of the first fluid can be reduced in a connection part between the first flow path device 2 and the second flow path device 3. It is sufficient that a size of the opening of the post-separation flow outlet 13 is 0.5 mm to 3 mm, for example, and preferably, about 2 mm, and a size of the opening of the first flow inlet 23 is 1.5 mm to 6 mm, for example, and preferably, about 5 mm.

The shape of the openings of the post-separation flow outlet 13 and the first flow inlet 23 is basically circular, but may be elliptical or rectangular such as a square, a rectangle, or a rhombus depending on the properties of the specific particles and the first fluid. When the shape of the openings is elliptical, if there is an other flow path near the opening, the minor axis of the opening may be set along the direction toward the other flow path, and the major axis of the opening may be set along the direction toward a margin around the opening, so that the influence of interference with other flow paths or the like can be reduced. Further, when the shape of the openings is a rhombus, it becomes easy to make a difference in the flow velocity of the first fluid between the central part and the peripheral part of the opening, so that the flow at the connection part may be controlled.

The post-separation flow outlet 13 and the first flow inlet 23 are basically arranged so as to be concentrically opposed to each other so that the centers are aligned with each other, but they may be arranged so as to be opposed to each other by shifting their centers. When the center of the post-separation flow outlet 13 is shifted toward the downstream side of the first flow path 16 with respect to the center of the first flow inlet 23, the first fluid tends to flow more easily to the downstream side of the first flow path 16 in connection with the flow of the second fluid, which will be described later.

The first flow path 16 further includes a vertical part 25 connected to the first flow inlet 23 (the second opening 18) and extending in the thickness direction and a planar part 26 connected to the vertical part 25 and extending to the second region 22 along a planar surface direction. The first flow path 16 includes the vertical part 25, thereby being able to reduce the retention of the first fluid in the connection part between the first flow path 16 and the separation flow path 4. The first flow path 16 includes the planar part 26, thereby being able to retain the first fluid in the planar part 26 in measurement of particles, thus a stable measurement can be achieved.

It is sufficient that a width of the vertical part 25 is 1.5 mm to 4 mm, for example, and a width of the planar part 26 is 1.5 mm to 6 mm, for example. It is sufficient that a length of the vertical part 25 is 0.5 mm to 1 mm, for example, and a height of the planar part 26 is 0.5 mm to 2 mm, for example.

FIG. 2 illustrates an example in which a sheet member 44 is arranged between the first flow path device 2 and the second flow path device 3, but since this sheet member 44 is not essential, the example illustrated in FIG. 5 illustrates an example in which the sheet member 44 is not used. By applying a silane coupling agent or the like to at least one of the first lower surface 11 of the first flow path device 2 or the second upper surface 19 of the second flow path device 3, the first flow path device 2 and the second flow path device 3 can be directly connected to each other.

Figure 6:
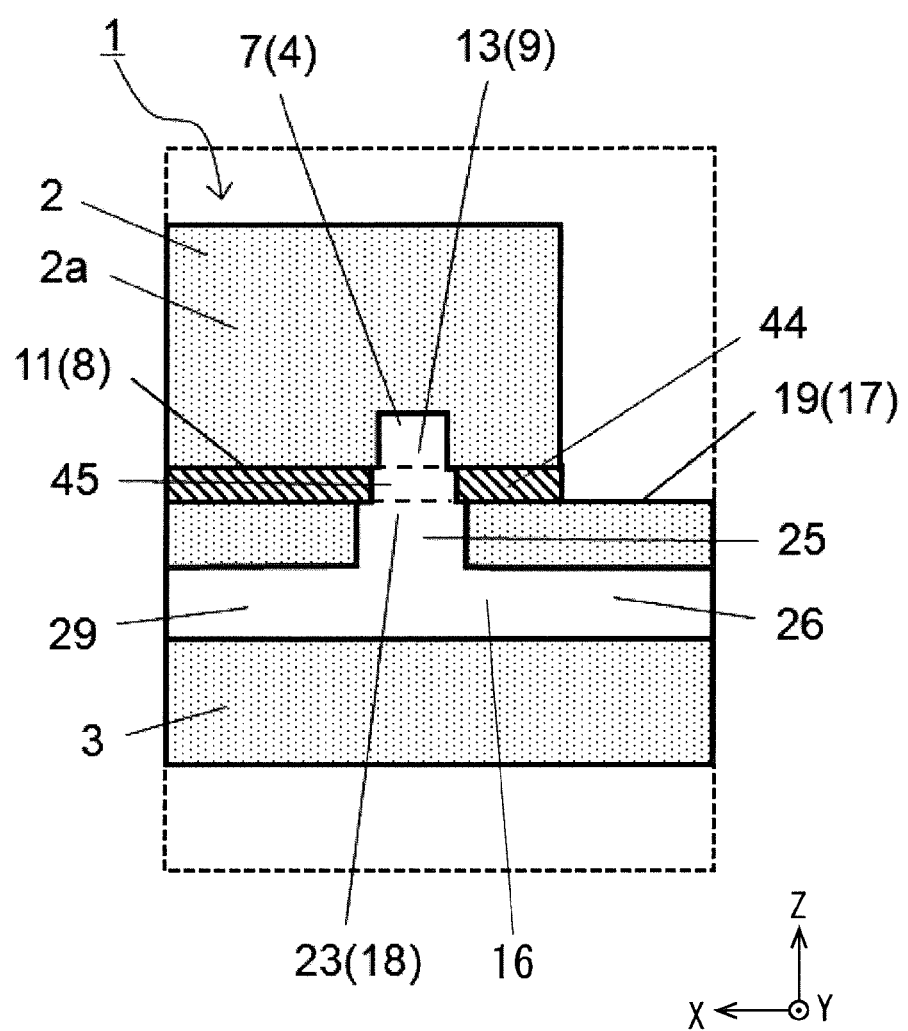
FIG. 6 illustrates a cross-sectional view showing a part of an example of the particle separating and measuring device according to an embodiment of the present disclosure.

On the other hand, as illustrated in FIG. 6 in the same cross-sectional view as in FIG. 5, the sheet member 44 may intervene between the first lower surface 11 of the first flow path device 2 and the second upper surface 19 of the second flow path device 3 as in the example illustrated in FIG. 2. That is, the particle separating and measuring device 1 may include the sheet member 44 arranged between the first flow path device 2 and the second flow path device 3. That is, the first flow path device 2 is placed on the second flow path device 3 via the sheet member 44, and the post-separation flow outlet 13 and the first flow inlet 23 may be connected via a through hole 45 of the sheet member 44. In this case, it is preferable that the size of the opening of the through hole 45 of the sheet member 44 be larger than the opening of the post-separation flow outlet 13 and smaller than the opening of the first flow inlet 23.

By interposing the sheet member 44 between the first flow path device 2 and the second flow path device 3, even when the first flow path device 2 and the second flow path device 3 are made of materials that are difficult to adhere to each other, the sheet member 44 can function as an intermediate layer for satisfactorily bonding the two, and the particle separating and measuring device 1 can be stably configured. Further, by setting the size of the opening of the through hole 45 interposed between the post-separation flow outlet 13 and the first flow inlet 23 to an intermediate size between the sizes of the upper and lower openings, the retention of the first fluid and the specific particles can be effectively prevented at the connection part between the first flow path device 2 and the second flow path device 3.

The sheet member 44 reduces leakage of the first fluid and the like from the bonding surface between the first flow path device 2 and the second flow path device 3, and functions as an intermediate layer for bonding the hardly-adhesive materials. The sheet member 44 may be formed of a material such as silicone or PDMS, for example. Further, by interposing the sheet member 44, a waviness of a surface of the first lower surface 11 and the second upper surface 19 as bonding surfaces can be absorbed. The sheet member 44 may include a plurality of through holes in addition to the space between the post-separation flow outlet 13 and the first flow inlet 23, if necessary. The plurality of through holes including these through holes 45 face the plurality of first openings 9 and the plurality of second openings 18. As a result, the fluid flows between the first flow path device 2 and the second flow path device 3 through these through holes.

It is sufficient that the thickness of the sheet member 44 is, for example, about 0.5 mm to 3 mm, and if it is about 2 mm, it is possible to satisfactorily absorb the waviness of the surface to be bonded, and the distance between the post-separation flow outlet 13 and the first flow inlet 23 does not unnecessarily increase. Further, it is possible to reduce the occurrence of cracks or the like when the first flow path device 2 and the second flow path device 3 are bonded to each other.

The size (area) of the sheet member 44 can be appropriately set as long as it is equal to or larger than the size required for bonding around the through hole 45 and equal to or smaller than the size of the first lower surface 11 of the first flow path device 2. Further, the sheet member 44 does not necessarily have to be one sheet, and may be a combination of a plurality of sheet members having a predetermined shape and size.

The first flow path device 2 and the second flow path device 3 in the present disclosure may be directly connected with the sheet member 44, or may be connected via an adhesive agent applied to an upper surface and a lower surface of the sheet member 44. It is sufficient that the adhesive agent is a photo-curable resin hardened by ultraviolet, a thermoplastic resin or the like, for example.

Figure 7:
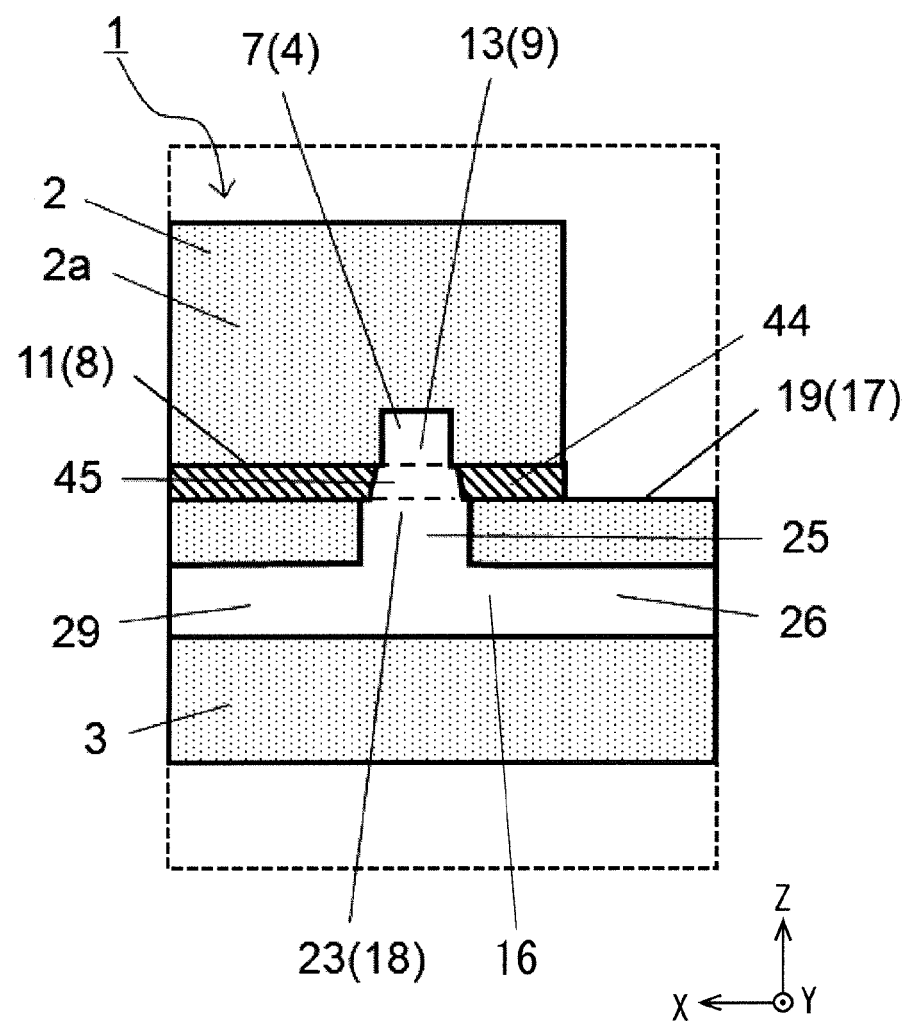
FIG. 7 illustrates a cross-sectional view showing a part of an example of the particle separating and measuring device according to an embodiment of the present disclosure.

Next, in the particle separating and measuring device 1 of the present disclosure, as illustrated in FIG. 7 in the same cross-sectional view as in FIG. 6, it is preferable that the size of the through hole 45 of the sheet member 44 increase from the post-separation flow outlet 13 side toward the first flow inlet 23 side. In this case, the opening on the post-separation flow outlet 13 side of the through hole 45 is larger than the opening of the post-separation flow outlet 13, and the opening on the first flow inlet 23 side of the through hole 45 is smaller than the opening of the first flow inlet 23. As a result, the retention of the flow of the first fluid from the post-separation flow outlet 13 to the first flow inlet 23 via the through hole 45 can be effectively prevented at the connection part. In this case, the cross-sectional shape of the inner wall of the through hole 45 may not necessarily be linear as illustrated in FIG. 7, and may have a shape becoming curvedly larger from the post-separation flow outlet 13 side toward the first flow inlet 23 side, that is, widened in so-called R-shape.

Next, in the particle separating and measuring device 1 of the present disclosure, as illustrated in FIG. 8 in the same cross-sectional view as in FIG. 5, the size of the post-separation flow outlet 13 and/or the first flow inlet 23 increases toward the downstream side of the fluid flow. That is, in the post-separation flow outlet 13, it is preferable that the inner diameter of the post-separation flow outlet 13 increase from the recovery flow path 7 side of the separation flow path 4 toward the opening of the post-separation flow outlet 13. In the first flow inlet 23, it is preferable that the inner diameter of the vertical part 25 increase from the opening of the first flow inlet 23 toward the planar part 26. The size of the post-separation flow outlet 13 and the first flow inlet 23 may be increased in either one or both toward the downstream side of the fluid flow. As a result, the retention of the first fluid at the connection part between the post-separation flow outlet 13 and the first flow inlet 23 can be effectively reduced. The sheet member 44 may be interposed between the post-separation flow outlet 13 and the first flow inlet 23 whose sizes are changed as described above, and the size of the through hole 45 of the sheet member 44 may be uniform in the length direction as in the example illustrated in FIG. 6, and may be increased from the post-separation flow outlet 13 side toward the first flow inlet 23 side as in the example illustrated in FIG. 7.

In the particle separating and measuring device 1 of the present disclosure, when the sheet member 44 arranged between the first flow path device 2 and the second flow path device 3 is provided, it is preferable that the hardness of the sheet member 44 be higher than the hardness of the first flow path device 2, and the hardness of the second flow path device 3 be higher than the hardness of the sheet member 44. As a result, the shape of the flow path formed in the relatively soft first flow path device 2 can be reliably held on the sheet member 44 serving as a flat and relatively hard base, between the first flow path device 2 and the sheet member 44. Further, between the second flow path device 3 and the sheet member 44, the adhesion between the second flow path device 3 serving as a relatively hard base and the sheet member 44 bonded to the second flow path device 3 can be increased so that the bonding between the two is strong. In this case, it is desirable that the bonding surface between the first flow path device 2 and the sheet member 44 and the bonding surface between the sheet member 44 and the second flow path device 3 have the same surface roughness. Specifically, the surface roughness of the bonding surfaces is preferably about 0.005 μm to 0.05 μm in terms of arithmetic mean roughness Ra.

At this time, regarding the hardness of each member, the hardness of the rubber molded product is generally evaluated by the International Rubber Hardness Degree (IRHD), and the resin molded product is evaluated by the Rockwell hardness. IRHD may be used for relative evaluation of hardness. For example, it is preferable that the hardness of the first flow path device 2 be equal to or greater than 30 and less than 80 in IRHD, the hardness of the sheet member 44 be about 80 in IRHD, and the hardness of the second flow path device 3 be more than 80 in IRHD. As a material having such a combination of hardness, for example, it is sufficient that the first flow path device 2 is made of PDMS, the sheet member 44 is made of a silicone sheet, and the second flow path device 3 is made of COP or PMMA. Specifically, with these materials, the hardness of the PDMS is about 30 in IRHD, the hardness of the silicone sheet is about 80 in IRHD, and the hardness of COP is more than 80 in IRHD (Rockwell hardness of about R50), so that this hardness combination is preferable.

As a method for measuring hardness, a method of pressing a non-sharp needle (pressing needle, indenter) into the surface of the target to be measured with a predetermined force, and measuring and quantifying the amount of deformation thereof may be applied. Regarding a force to push the needle, there are durometer hardness using a spring and International Rubber Hardness Degree (IRHD) using a constant load such as a weight. The durometer hardness is widely used in general since a measuring instrument is simple, so it is sufficient to use this.

Figure 9:
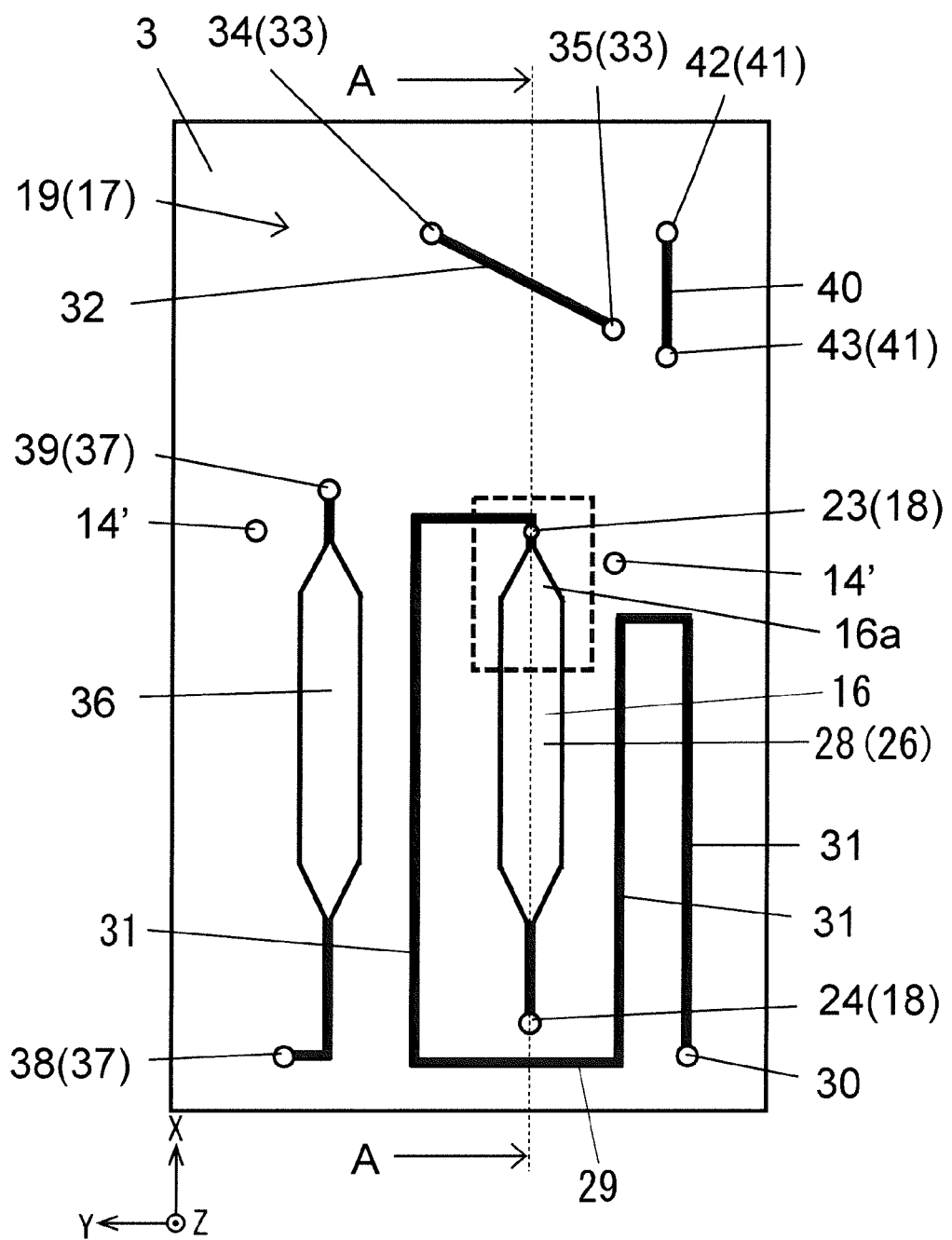
FIG. 9 illustrates a plan view showing an example of a second flow path device in the particle separating and measuring device according to an embodiment of the present disclosure.
Figure 10:
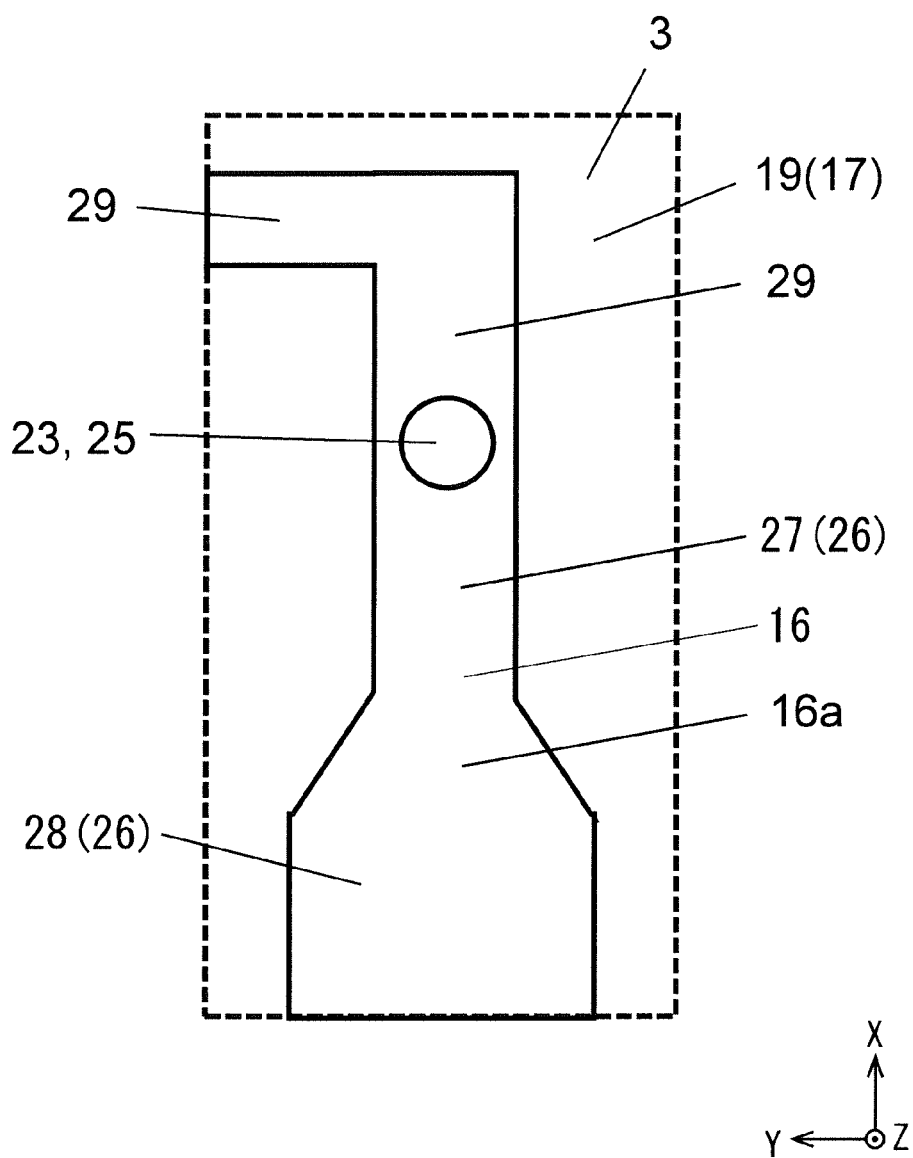
FIG. 10 illustrates a plan view showing a part of an example of the second flow path device in the particle separating and measuring device according to an embodiment of the present disclosure.

FIGS. 9 and 10 schematically illustrate an example of the second flow path device 3 used in the particle separating and measuring device 1. FIG. 9 is a plan view of the second flow path device 3 viewed from above. FIG. 10 is an enlarged plan view of a broken line section in FIG. 9. The A-A line in FIG. 9 is at the same position as the A-A line in FIG. 1.

It is preferable that at least a part of the planar part 26 of the first flow path 16 connected to the vertical part 25 have a width larger than the width of the vertical part 25. As a result, the retention of the first fluid can be reduced at the connecting part between the planar part 26 and the vertical part 25.

The planar part 26 may further include a first planar part 27 connected to the vertical part 25 and a second planar part 28 connected to the first planar part 27 and having a width larger than the first planar part 27. It is preferable that the first planar part 27 and the second planar part 28 be connected by a width increasing part 16a in which the width of the flow path increases toward the downstream side of the fluid flow. That is, it is preferable that the second flow path device 3 includes the width increasing part 16a in which the width of the flow path increases toward the downstream side of the flow of the first fluid, between the first flow inlet 23 and the second planar part 28 located in the second region 22 and used as a measurement unit of the first flow path 16. As a result, a flow that spreads in the width direction occurs in the first fluid in the width increasing part 16a, and thereby, specific particles contained in the first fluid are dispersed, so that the bias of the specific particles can be reduced during measurement. As a result, for example, the first particles P1 separated and recovered by the first flow path device 2 can be easily diffused in the second planar part 28.

It is sufficient that a width of the first planar part 27 is 0.5 mm to 3 mm, for example, and a width of the second planar part 28 is 1 mm to 5 mm, for example. It is sufficient that a width of the second planar part 28 is 2 times to 10 times that of the first planar part 27, for example. In the present disclosure, the width increasing part 16a at the connecting part of the first planar part 27 and the second planar part 28 is gradually increased. That is, it can be said that the shape of the width increasing part 16a is a reverse taper shape when viewed in the width direction. It is sufficient that the spread angle of the reverse taper shape in this case is 20° to 40° on one side with respect to the center line of the width of the planar part 26 (the first planar part 27 and the second planar part 28) so that the width of the planar part 26 is widened. It is sufficient that the length of the reverse taper portion is about 3 mm to 5 mm.

It is preferable that the second planar part 28 have a height larger (is higher) than the first planar part 27. As illustrated in FIG. 11 in the same cross-sectional view as in FIG. 2, it is preferable that the second flow path device 3 includes a height increasing part 16b in which the height of the flow path increases toward the downstream side of the flow of the first fluid, between the first flow inlet 23 and the second planar part 28 located in the second region 22 and used as a measurement unit of the first flow path 16. As a result, a flow that spreads in the height direction occurs in the first fluid in the height increasing part 16b, and thereby, specific particles contained in the first fluid are dispersed, so that the bias of the specific particles can be reduced during measurement. The height of the flow path is increased in relatively short length, so that a vortex movement occurs in the fluid flow and agitation of specific particles is facilitated. As a result, the separated specific particles, for example, the first particles P1 can be easily diffused.

It is sufficient that the height of the first planar part 27 is 0.2 mm to 1 mm, for example. It is sufficient that the height of the second planar part 28 is 1 mm to 5 mm, for example. In the present disclosure, the height increasing part 16b at the connecting part of the first planar part 27 and the second planar part 28 is gradually increased. That is, it can be said that the shape of the height increasing part 16b is a reverse taper shape when viewed in the height direction. At this time, for example, it is sufficient that the height of the first planar part 27 is 0.5 mm, the height of the second planar part 28 is 1 mm, and the angle of the reverse taper is at about 45° so that the height of the height increasing part 16b is widened.

When the width increasing part 16a and the height increasing part 16b are set in combination, it is preferable to provide the height increasing part 16b first on the upstream side of the flow path and to provide the width increasing part 16a immediately after the height increasing part 16b. It is preferable that both be arranged as close to each other as possible. This is because, since the size of the flow path is wider (larger) in the width direction than in the height direction, first, spreading the dimension in the height direction and stirring up and down with the width narrow, and then spreading the dimension in the width direction and stirring left and right enables more uniform stir. On the other hand, if the dimension is widened in the width direction first, the influence and effect of stirring in the height direction tend to be small.

The second flow path device 3 may further include, in addition to the first flow path 16, a third flow path 29 connected to the first flow path 16. It is preferable that the third flow path 29 be connected to the planar part 26 of the first flow path 16. The third flow path 29 has a function of sweeping away the fluid retained in the planar part 26 by flowing gas, for example. As a result, the retention of the fluid in the first flow path 16 can be reduced.

In the second flow path device 3 in the present disclosure, as illustrated in FIGS. 9 and 10, the third flow path 29 is connected to the connection part between the vertical part 25 and the planar part 26 in the first flow path 16.

One end of the third flow path 29 is connected to the first flow path 16. The other end of the third flow path 29 serves as a third opening 30 located in the pair of second upper and lower surfaces 17. In other words, the third flow path 29 includes the third opening 30 located in one of the pair of second upper and lower surfaces 17 (in the present disclosure, the second upper surface 19). The third opening 30 is an opening through which an extrusion fluid, for example, gas or the like for sweeping away the fluid from the second planar part 28 of the planar part 26 flows in.

At least part of the third flow path 29 connected to the first flow path 16 may extend along an extension direction of the planar part 26 (second planar part 28) of the first flow path 16 as illustrated in FIG. 9.

It is preferable that at least part of the third flow path 29 connected to the first flow path 16 have the same shape as at least part of the first flow path 16 connected to the third flow path 29. As a result, a level difference occurring between the first flow path 16 and the third flow path 29 and the retention of the fluid in the level difference in the connection part can be reduced.

As illustrated in FIG. 9, it is preferable that the third flow path 29 includes a plurality of linear parts 31 each extending in predetermined one direction and arrayed in a direction intersecting with one direction. The third flow path 29 includes the plurality of linear parts 31, thereby being able to reduce the fluid flowing back from the first flow path 16 and leaked from the third opening 30.

The pre-separation flow inlet 12 of the first opening 9 in the first flow path device 2 may be arranged in a surface (the first lower surface 11 in the present disclosure) similar to that of the post-separation flow outlet 13 of the first opening 9.

In this case, the sample flows into the first flow path device 2 from below (negative side of the Z axis direction). As a result, the second particles P2 can be sunk when a specific gravity of the second particles P2 is larger than that of the first particles P1, thus the particles can be separated easily.

The second flow path device 3 may further include a fourth flow path 32 different from the first flow path 16 and the third flow path 29 as illustrated in FIG. 9. The fourth flow path 32 may include a plurality of fourth openings 33 located in either surface or both surfaces of the pair of second upper and lower surfaces 17. The fourth flow path 32 can function as a flow path in which the sample before the specific particles are separated flows. As a result, the sample is flowed into the fourth flow path 32 of the second flow path device 3 before flowed into the first flow path device 2, thus a foreign material and the like which have been mixed into the sample and the like to flow can be previously reduced.

The plurality of fourth openings 33 include a fourth flow inlet 34 and a fourth flow outlet 35. The fourth flow inlet 34 is an opening through which the sample flows into the fourth flow path 32. The fourth flow outlet 35 is an opening through which the sample flows from the fourth flow path 32. The fourth flow inlet 34 is opened so that the sample can flow into the fourth flow inlet 34 from the outside, and the fourth flow outlet 35 is connected to the pre-separation flow inlet 12 of the first flow path device 2.

The fourth flow inlet 34 and the fourth flow outlet 35 may be located in the second upper surface 19. In that case, an operation such as an external connection for allowing the sample to flow in can be performed from above the second flow path device 3. In the present disclosure, the fourth flow inlet 34 is located in the same surface as that of the first flow inlet 23. In the present disclosure, the fourth flow outlet 35 is located in the same surface as that of the first flow inlet 23. The fourth flow inlet 34 is located in the same surface as that of the third opening 30.

The second flow path device 3 may further include a second flow path 36 different from the first flow path 16, the third flow path 29, and the fourth flow path 32 as illustrated in FIG. 9. While the first flow path 16 is a flow path for flowing the first fluid containing the specific particles separated and recovered in the first flow path device 2, the second flow path 36 is a flow path for flowing the second fluid not containing the specific particles and serves as a flow path for flowing the second fluid for comparison or correction at the time of measuring of the first fluid, for example. As the second fluid, fluid that is the same as the first fluid and does not contain specific particles may be used, or fluid that is different from the first fluid may be used. As a result, it is possible to measure the first flow path 16 and the second flow path 36 in sequence every time the specific particles are measured to estimate the number of specific particles in accordance with a difference of light intensity of the flow paths 16 and 36, thus an influence of deterioration of an optical sensor can be reduced.

The second flow path 36 includes a plurality of fifth openings 37 located in the pair of second upper and lower surfaces 17. The fifth openings 37 include a second flow inlet 38 and a second flow outlet 39. The second flow inlet 38 is an opening through which the second fluid flows into the second flow path 36. The second flow outlet 39 is an opening through which the second fluid flows out from the second flow path 36. The second flow path 36 includes a portion having the same shape as the second planar part 28 of the first flow path 16 as a measurement unit.

The second flow inlet 38 of the plurality of fifth openings 37 is located in the same surface as that of the third opening 30. As a result, an operation of flowing in and out of the second fluid can be performed on the same surface from an upper side of the second flow path device 3. It is preferable that the second flow outlet 39 be arranged in the second lower surface 20.

The second flow path device 3 may further include a sixth flow path 40 different from the first flow path 16, the third flow path 29, the fourth flow path 32, and the second flow path 36. The sixth flow path 40 includes a plurality of sixth openings 41 located in either surface or both surfaces of the pair of second upper and lower surfaces 17. The plurality of sixth openings 41 include a sixth flow inlet 42 and a sixth flow outlet 43. The sixth flow inlet 42 is an opening through which a fluid for a pressing flow flows into the sixth flow path 40. The sixth flow outlet 43 is an opening through which a fluid for a pressing flow flows out from the sixth flow path 40. The sixth flow inlet 42 is located so that the fluid can flow into the sixth flow path 40, and the sixth flow outlet 43 is connected to the pressing flow inlet 15 of the first flow path device 2.

The third flow path 29, the fourth flow path 32, the second flow path 36, and the sixth flow path 40 can be formed in the manner similar to the first flow path 16.

(Particle Separating Apparatus)

Next, a particle separating apparatus in the particle separating and measuring apparatus of the present disclosure will be described. The particle separating apparatus of the present disclosure includes the first flow path device 2 that is a particle separating device, a first pump for flowing a sample into a pre-separation flow inlet 12, and a second pump for flowing a fluid into the pressing flow inlet 15. The particle separating device is the first flow path device 2 described above, and the first pump is connected to the pre-separation flow inlet 12 of the first flow path device 2 by, for example, a first tube. The sample sent from the first pump flows into the pre-separation flow inlet 12 of the first flow path device 2 through the first tube. The second pump is connected to the pressing flow inlet 15 of the first flow path device 2 by, for example, a second tube. The fluid sent from the second pump flows into the pressing flow inlet 15 of the first flow path device 2 through the second tube. As a result, as described above, specific particles, for example, the first particles P1 can be separated and recovered from the sample by the main flow path 5 and the plurality of branch flow paths 6.

As the first pump and the second pump, various known pumps can be used as long as they can deliver fluids. It is desirable that the first pump have a function of allowing a small amount of a fluid containing particles, for example, blood, to flow into the pre-separation flow inlet 12 of the first flow path device 2 at a constant flow rate. It is desirable that the second pump have a function of allowing a fluid for generating a pressing flow, for example, Phosphate Buffered Saline (PBS), to flow into the pressing flow inlet 15 of the first flow path device 2 at an appropriate flow amount, flow rate, and pressure. For these first pump and second pump, for example, a syringe pump can be preferably used. Other pumps such as an electroosmotic flow pump, a peristaltic pump, and a gas pump can also be used.

The first tube and the second tube can be formed by using tubes made of various known materials depending on the fluid used. When the sample is blood and the fluid is PBS, for example, a silicone tube can be preferably used. These tubes are not essential members, and, for example, when the first flow path device 2 is directly connected to the first pump and the second pump, or when they are connected via an adapter, these tubes may not be provided.

(Particle Separating and Measuring Apparatus)

Next, a particle separating and measuring apparatus of the present disclosure including the particle separating and measuring device of the present disclosure will be described.

FIGS. 12 and 13 schematically illustrate a particle separating and measuring apparatus 47. FIG. 12 is a cross-sectional view of the particle separating and measuring apparatus 47 viewed from the same viewpoint as that in FIGS. 2 and 11. Note that some of the symbols similar to those in FIGS. 2 and 11 are omitted. FIG. 13 schematically illustrates an example of the overall configuration of the particle separating and measuring apparatus 47 in a block diagram.

The particle separating and measuring apparatus 47 includes the particle separating and measuring device 1 and an optical sensor 48. The optical sensor 48 includes a light-emitting element 49 and a light receiving element 50. As a result, first flow path device 2 of the particle separating and measuring device 1 can separate the required specific particles (for example, the first particles P1) from the sample. Then, the specific particles flowing to the first flow path 16 (second planar part 28) of the second flow path device 3 of the particle separating and measuring device 1 is irradiated with light from, the light-emitting element 49 of the optical sensor 48, and the light receiving element 50 of the optical sensor 48 receives the light passing through the first flow path 16 (second planar part 28), thus the particles can be measured. Specifically, the light passing through the first flow path 16 is scattered, reflected or absorbed by the particles (the first particles P1) in the first fluid, thus the light intensity decreases. The light is received, and a standard curve indicating a relationship between the sample including the particles, the number of which is already known, and an attenuation amount of the light is previously prepared. An attenuation amount of the light measured by the particle separating and measuring apparatus 47 is checked against the standard curve, thus the particles in the sample can be measured.

The particle separating and measuring apparatus 47 of the present disclosure includes: the particle separating and measuring device 1 of the present disclosure described above; the optical sensor 48 that irradiates the measurement unit of the first flow path 16 and the measurement unit of the second flow path 36 of the particle separating and measuring device 1 with light, and receives light that has passed through the measurement unit of the first flow path 16 and the measurement unit of the second flow path 36; and a control unit that measures the specific particles by comparing intensity of light, obtained by the optical sensor 48, that has passed through the first flow path 16 and intensity of light, obtained by the optical sensor 48, that has passed through the second flow path 36.

It is sufficient that the light-emitting element 49 is a light emitting diode (LED), for example. It is sufficient that the light receiving element 50 is a photo diode (PD), for example. The optical sensor 48 includes a semiconductor substrate in which the PD of the light receiving element 50 is formed by including a region of one conductivity type and a region of the other conductivity type on an upper surface, for example, and includes an LED of the light-emitting element 49 including a plurality of semiconductor layers laminated on the semiconductor substrate.

A mirror member (reflection member) 51 is arranged in the second region 22 of the second upper surface 19 of the second flow path device 3 in the particle separating and measuring device 1 of the particle separating and measuring apparatus 47 of the present disclosure. The light-emitting element 49 and the light receiving element 50 of the optical sensor 48 are located on the second lower surface 20 side of the second flow path device 3. Accordingly, the light receiving element 50 of the optical sensor 48 can receive the light emitted from the light-emitting element 49, passing through the first flow path 16 (second planar part 28), and reflected from the mirror member 51. The mirror member 51 may be formed of a material such as aluminum or gold, for example. The mirror member 51 can be formed by an evaporation method, a sputtering method or the like, for example, and also can be formed by arranging a metal foil or the like.

The particle separating and measuring apparatus 47 further includes a first supply unit 52 supplying the sample, a second supply unit 53 supplying the fluid of the pressing flow, a third supply unit 54 supplying the extrusion fluid, and a fourth supply unit 55 supplying the second fluid as the correction fluid, all of which are connected to the particle separating and measuring device 1. The first supply unit 52 is connected to the fourth flow inlet 34. The second supply unit 53 is connected to the sixth flow inlet 42. The third supply unit 54 is connected to the third opening 30. The fourth supply unit 55 is connected to the second flow inlet 38. The particle separating and measuring apparatus 47 includes a control unit (not shown), and the control unit controls the first supply unit 52, the second supply unit 53, the third supply unit 54, the fourth supply unit 55, and the optical sensor 48.

According to the particle separating and measuring apparatus 47 of the present disclosure, since the particle separating and measuring device 1 of the present disclosure is provided, it is possible to separate specific particles from the sample and perform measurement successfully and stably.

As described above, according to the particle separating and measuring device and the particle separating and measuring apparatus of the present disclosure, since the post-separation flow outlet of the first flow path device as the particle separating device and the first flow inlet of the second flow path device as the particle measuring device are connected to each other so as to face each other, and the size of the opening of the first flow inlet is larger than the size of the opening of the post-separation outlet, it is possible to reduce the occurrence of problems such as retention of the specific particles, separated by the first flow path device, at the connection part between the first flow path device and the second flow path device. Therefore, it is possible to allow the first liquid containing the specific particles separated by the first flow path device to smoothly flow into the second flow path device, and efficiently perform stable measurement.

The present invention is not limited to the embodiments described above, however, various alternation and modifications, for example, should be possible within the scope of the present disclosure.

Figure 14:
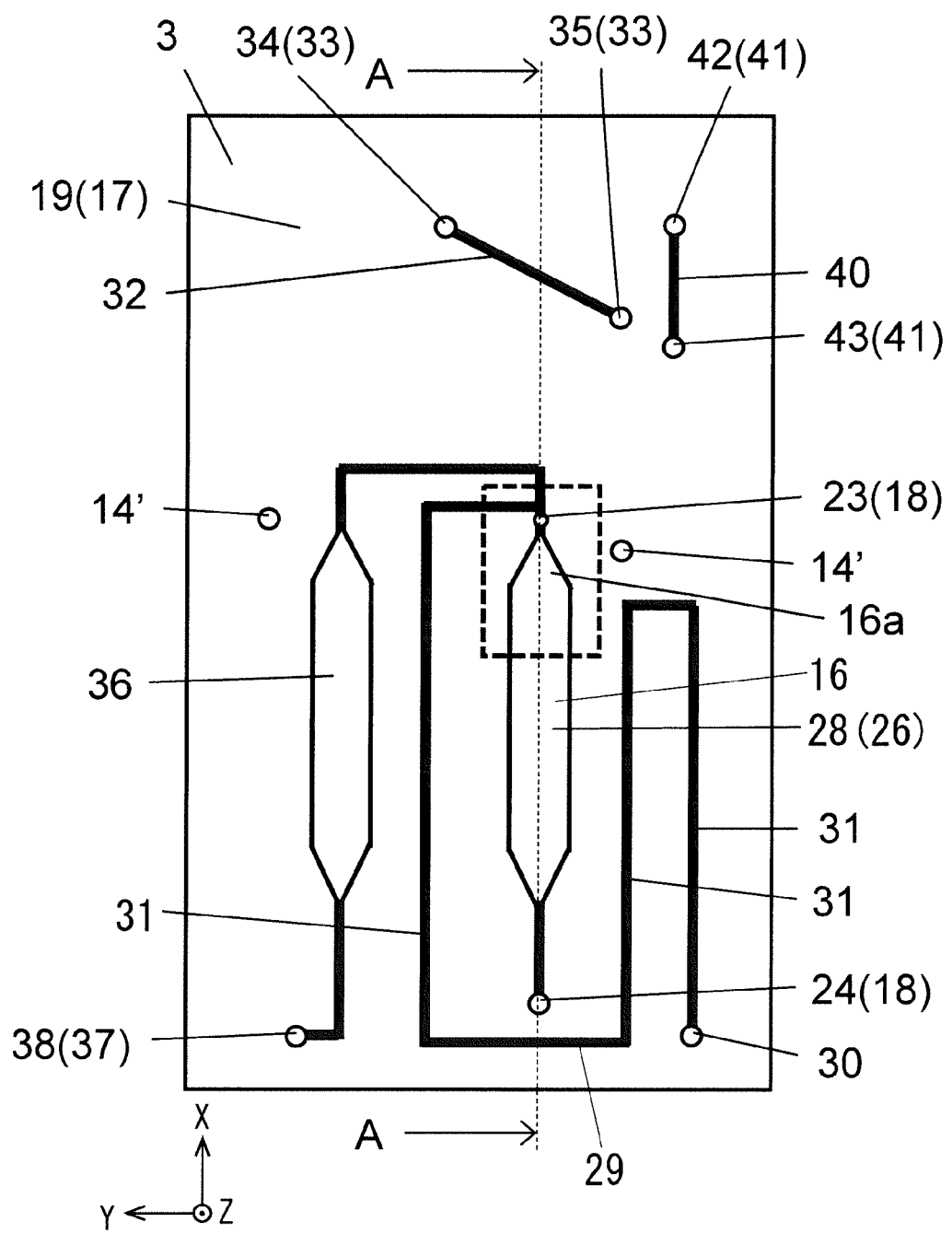
FIG. 14 illustrates a plan view showing an example of a second flow path device in the particle separating and measuring device according to an embodiment of the present disclosure.
Figure 15:
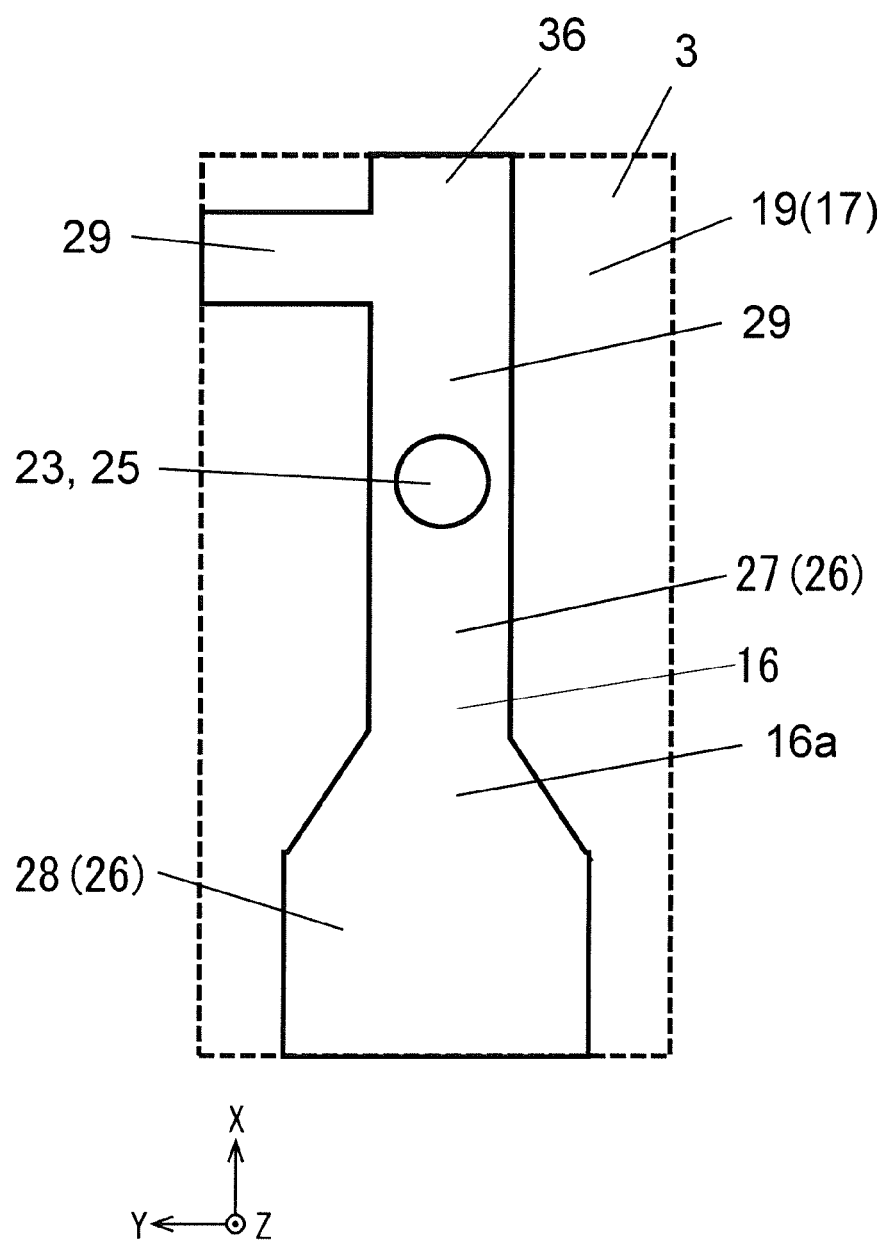
FIG. 15 illustrates a plan view showing a part of an example of the second flow path device in the particle separating and measuring device according to an embodiment of the present disclosure.

The above embodiments describe the example that one end of the second flow path 36 includes the second flow outlet 39, however, as illustrated in FIGS. 14 and 15, one end of the second flow path 36 may be connected to the first flow path 16. In this case, the second fluid in the second flow path 36 can be injected into the first flow path 16, thus the above configuration has an effect that a concentration of specific particles such as white blood cells contained in the first fluid in the first flow path 16 can be diluted. FIGS. 14 and 15 are illustrated with the viewpoint similar to that in FIGS. 9 and 10, and detailed description thereof is omitted.

The above embodiments describe the example that the second flow path device 3 includes the second flow path 36 and the sixth flow path 40, however, the second flow path 36 may function as the sixth flow path 40. That is to say, the second flow path 36 and the sixth flow path 40 may constitute one flow path to be connected to the separation flow path 4 (pressing flow inlet 15).

The invention claimed is:

1. A particle separating and measuring device comprising:
a first flow path device having a plate-like shape and including a pre-separation flow inlet through which a fluid flows in that contains specific particles to be separated, a main flow path connected to the pre-separation flow inlet, a plurality of branch flow paths each connected to the main flow path, and a post-separation flow outlet through which a first fluid flows out that contains the specific particles that have been separated; and
a second flow path device having a plate-like shape and having a first region on which the first flow path device is placed, and a second region that serves as a measurement region for the specific particles, the second flow path device including a first flow inlet through which the first fluid flows in, a second flow inlet through which a second fluid not containing the specific particles flows in, a first flow path connected to the first flow inlet and through which the first fluid passes, and a second flow path connected to the second flow inlet and through which the second fluid passes, wherein the first flow path and the second flow path are arranged in the second region;
wherein the post-separation flow outlet is arranged in a lower surface of the first flow path device, and is placed on the second flow path device to face and connect to the first flow inlet that is arranged in an upper surface of the first region of the second flow path device, and
a size of an opening of the first flow inlet is larger than a size of an opening of the post-separation flow outlet.

2. The particle separating and measuring device according to claim 1,
wherein the first flow path device is placed on the second flow path device via a sheet member, and the post-separation flow outlet and the first flow inlet are connected via a through hole of the sheet member, and
a size of an opening of the through hole of the sheet member is larger than the size of the opening of the post-separation flow outlet and smaller than the size of the opening of the first flow inlet.

3. The particle separating and measuring device according to claim 2,
wherein the size of the through hole increases from the post-separation flow outlet toward the first flow inlet.

4. The particle separating and measuring device according to claim 1,
wherein the size of the post-separation flow outlet and/or the size of the first flow inlet increases toward a downstream side of a fluid flow.

5. The particle separating and measuring device according to claim 2,
wherein a hardness of the sheet member is higher than a hardness of the first flow path device, and a hardness of the second flow path device is higher than the hardness of the sheet member.

6. The particle separating and measuring device according to claim 1,
wherein the second flow path device includes a width increasing part in which a width of a flow path increases toward a downstream side of a flow of the first fluid, between the first flow inlet and a measurement unit of the first flow path.

7. The particle separating and measuring device according to claim 1,
wherein the second flow path device includes a height increasing part in which a height of a flow path increases toward a downstream side of a flow of the first fluid, between the first flow inlet and a measurement unit of the first flow path.

8. A particle separating and measuring apparatus comprising:
the particle separating and measuring device according to claims 1;
an optical sensor that irradiates a measurement unit of the first flow path and a measurement unit of the second flow path of the particle separating and measuring device with light, and receives light that has passed through the measurement unit of the first flow path and the measurement unit of the second flow path; and
a control unit that measures the specific particles by comparing intensity of light, obtained by the optical sensor, that has passed through the measurement unit of the first flow path and intensity of light, obtained by the optical sensor, that has passed through the measurement unit of the second flow path.

* * * * *